United States Patent [19]

Meilland

[11] Patent Number: Plant 5,958

[45] Date of Patent: Apr. 28, 1987

[54] ROSE PLANT—MEIPINJID VARIETY

[75] Inventor: Marie-Louise Meilland, Antibes, France

[73] Assignee: The Conard-Pyle Company, West Grove, Pa.

[21] Appl. No.: 763,996

[22] Filed: Aug. 9, 1985

[51] Int. Cl.[4] ..... A01H 5/00

[52] U.S. Cl. ..... Plt./9

[58] Field of Search ..... Plt./9

*Primary Examiner*—James R. Feyrer

*Attorney, Agent, or Firm*—Burns, Doane, Swecker & Mathis

[57] ABSTRACT

A new and distinct variety of rose plant of the Miniature Class is provided which resulted as a bud mutation of the Meijidiro variety. The new variety has attractive double flowers which are of a deeper hue of pink than its parent. Also, the new variety exhibits a more vigorous growth habit than its parent. Plants of the new variety can be grown to advantage in the landscape as a small flowering woody plant or in pots indoors.

15 Drawing Figures

SUMMARY OF THE INVENTION

The new variety resulted from the selective study of miniature rose plants formed by the budding in France of the Meijidiro variety (U.S. Plant Pat. No. 4,961).

During the course of the selective study, large numbers of plants propagated from the Meijidiro variety were carefully observed and evaluated. The new variety of the present invention was selected because of its distinctive characteristics (discussed hereafter) and is believed to be a bud mutation of unknown causation.

The new variety readily can be distinguished from the Meijidiro variety because the blossoms are of a substantially deeper hue of pink and the overall plant exhibits a more vigorous growth habit.

It has been found that plants of the new variety are particularly well-adapted to be grown in the landscape as a small flowering woody plant. Also, plants of the new variety are well-adapted to be grown as an attractive flowering pot plant under greenhouse culture conditions.

Extensive testing has confirmed the behavior and characteristics of the new variety. The new variety can be propagated well by budding, grafting, or through the rooting of cuttings. The new variety exhibits an excellent propensity to form roots on cuttings. After more than ten generations of propagation, it has been determined that the new variety is, indeed, quite stable with the percentage of reversion back to the parent being less than one percent.

The new variety has been named the Meipinjid variety.

BRIEF DESCRIPTION OF THE PHOTOGRAPH

The accompanying photograph shows, as nearly true as it is reasonably possible to make the same, in a color illustration of this character, typical specimens of plant parts of the new variety.

DETAILED DESCRIPTION

Figures 1, 2, 3, 4, 5, 6, 7, 8, 9, 10, 11, 12, 13, 14, 15:
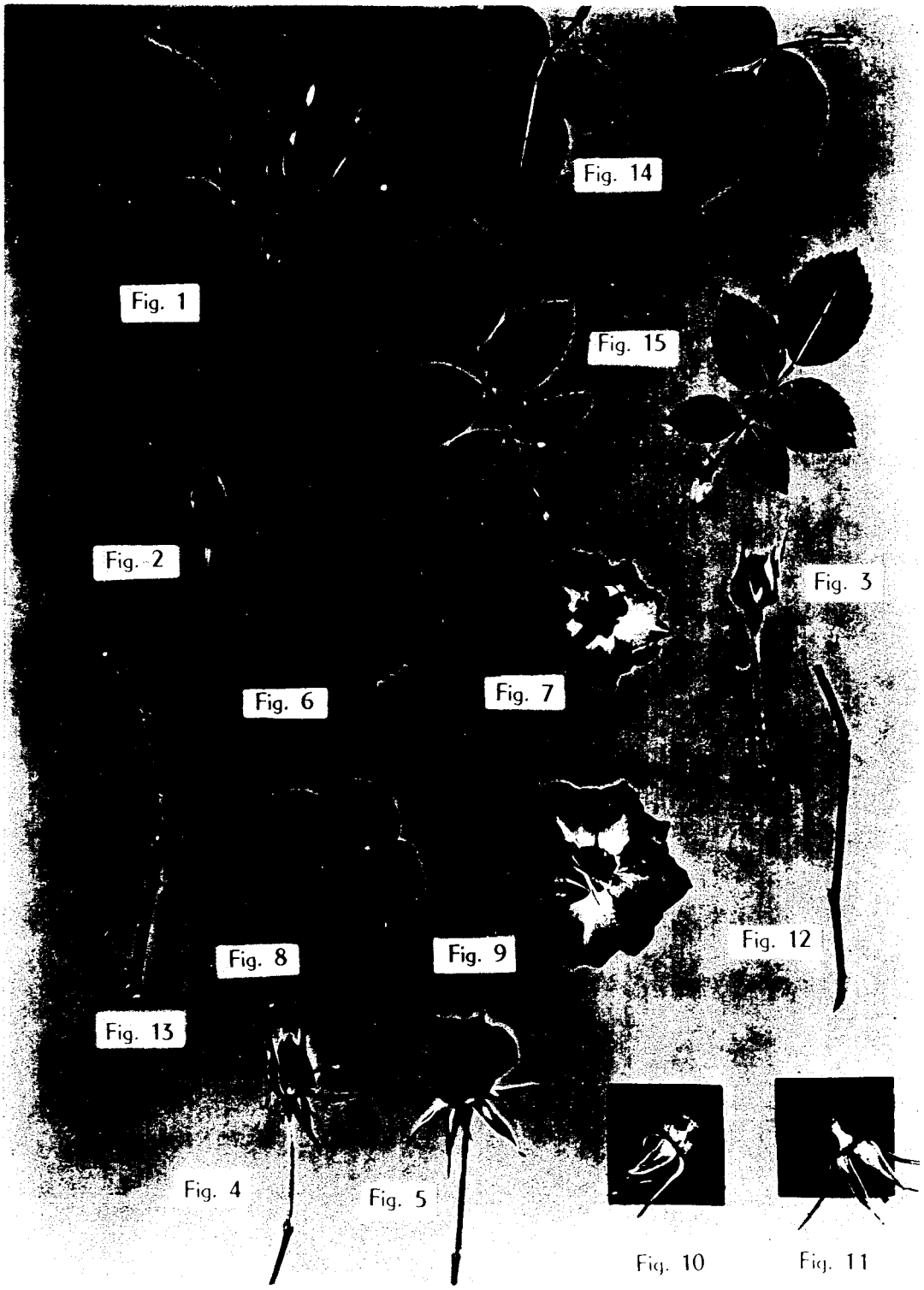
FIG. 1 illustrates a specimen of a young shoot with buds before much opening of the sepals has taken place.
FIG. 2 illustrates a specimen of a bud before the opening of the sepals.
FIG. 3 illustrates a specimen of a bud as the sepals open.
FIG. 4 illustrates a specimen of a bud as the petals begin to open.
FIG. 5 illustrates a specimen of a flower early in the course of opening.
FIG. 6 illustrates a specimen of a partially open flower — plan view — obverse.
FIG. 7 illustrates a specimen of a partially open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of leaves with three leaflets with a typical under surface being shown on the left and a typical upper surface being shown on the right.
FIG. 15 illustrates specimens of leaves with five leaflets with a typical upper surface being shown on the left and a typical under surface being shown on the right.

The chart used in the identification of the colors is that of The Royal Horticultural Society (R.H.S. Colour Chart). The terminology preceding the numbered references has been added to designate in common terms, the corresponding colors.

Class: Miniature.

Plant:

*Height.*—Approximately 30 cm. on average.

*Habit.*—Bushy.

Branches:

*Color.*—Young stems: light green, Yellow-Green Group 144A, with somewhat reddish shading at times. Mature wood: bronzed green, Yellow-Green Group 146A.

*Thorns.*—Shape: Upper edge: straight, very thin. Under edge: slightly concave. Size: medium. Quantity: fairly numerous. Color (on young stems): reddish. (on mature wood): straw, then becoming havana brown.

Leaves:

*Stiples.*—Adnate, pectinate, rather narrow and linear.

*Petioles.*—Inner surface: grooved, reddish brown (young foiliage); medium green (adult foliage — edges more or less gladular). Outer surface: reddish (young foliage); light green (adult foliage). This side carries a few hooked thorns.

*Leaflets.*—Number: 3, 5, and 7 (most frequently). Shape: elliptic — slightly lanceolate. Margins: serrate. Texture: leathery. General effect: small, dense and dull in appearance. Color (young foliage): upper surface: Yellow-Green Group 146A with bronze shading. Under surface: medium green, Yellow-Green Group 147B. Color (adult foliage): Upper surface: dark green, Yellow-Green Group 147A. Under surface: light green, Yellow-Green Group 147C.

Inflorescense:

*Number of flowers.*—Pauciflorous (1 to 3 per stem).

*Peduncle.*—Straight, rigid, slightly spotted with reddish brown. It is slightly glandular and bears a few hooked thorns. It is sometimes very lightly grooved. Length: approximately 2.3 cm. on average.

*Sepals.*—Upper surface: tomentous, greenish, more or less spotted with reddish coloration. Under surface: light green, more or less spotted with reddish coloration and more or less gladular. The outside sepals have slightly appendiculate edges.

*Buds.*—Shape: conical before the opening of the sepals. Length: approximately 1.1 cm on average, not counting the calyx, at the opening of the sepals. Size: small.

*Flower.*—Form: double. Diameter: approximately 4.8 cm on average. Color when one-fourth open: Red Group 53D. Color when one-half open:

Upper surface: between Red Group 52A and 52B. Under surface: between Red Group 52B and 52C. Color when fully open: Upper surface: Red Group 52B. Under surface: between Red Group 52B and 52C. Fragrance: very light. Lasting quality: very long. Corolla — petals: Texture: consistent. Form: round, slightly flattened with a small point at the top. The petals become cuneiform at the center and tend to fold along a median line. The unguis is small and whitish on both faces. Number: approximately 40 on average, as well as approximately 15 petals which are not completely formed at the center of the bloom. Stamens — number: approximately 49 on average. Anthers: normal, yellow. Filaments: yellow base, very lightly tinted with fuschia top. Pistils — number: approximately 36 on average. Stigmas: normal, yellowish. Styles: free, straw with fuschia top, more or less twisted and tomentous; irregular heights. Receptacle: light green, more or less spotted with reddish brown; at the dehiscence of the anthers and in longitudinal cross-section, it is very narrow and funnel-shaped.

Development:

*Vegetation.*—More vigorous than Meijidiro variety.

*Blossoming.*—Abundant.

*Fruiting ability.*—Very low.

*Resistance to diseases.*—Good.

I claim:

1. A new and distinct variety of Miniature rose plant which originated as a bud mutation of the Meijidiro variety, substantially as shown and described, having flowers which are of deeper hue of pink and a more vigorous growth habit than the Meijidiro variety.

* * * * *